United States Patent [19]

Van Poucke et al.

[11] 4,131,735
[45] Dec. 26, 1978

[54] PREPARATION OF α-ACYLACETAMIDES USING TETRAMETHYL GUANIDINE CONDENSING AGENT

[75] Inventors: Raphäel K. Van Poucke, Berchem; Freddy C. Baeyens, Wommelgem; Paul A. Mortelmans, Wilrijk, all of Belgium

[73] AGFA-GEVAERT, N.V., Mortsel, Belgium

[21] Appl. No.: 635,063

[22] Filed: Nov. 25, 1975

[51] Int. Cl.$^2$ .................. C07D 235/00; C07D 239/72; C07D 253/06; C07D 253/04
[52] U.S. Cl. .................................... 544/267; 544/265; 544/266; 544/287; 560/13; 260/302 R; 260/308 R; 260/308 A; 260/559 D; 260/561 K; 260/562 K; 260/558 P; 260/564 A
[58] Field of Search .......... 260/561 K, 562 K, 558 P, 260/564 A, 559 D, 251 R, 251 A, 251 QA, 308 R, 308 A, 302 R; 560/13; 544/265, 266, 267, 287

[56] References Cited

U.S. PATENT DOCUMENTS

| | | | |
|---|---|---|---|
| 2,009,397 | 7/1935 | Goldstein | 260/562 K X |
| 2,368,302 | 1/1945 | Jennings | 260/562 K X |
| 2,396,917 | 3/1946 | Hanford et al. | 260/562 K X |
| 2,416,738 | 3/1947 | Cashion | 260/562 K |
| 2,591,470 | 4/1952 | Schmid et al. | 260/562 K X |
| 3,265,506 | 8/1966 | Weissberger et al. | 260/562 K |
| 3,277,155 | 10/1966 | Loria et al. | 260/561 K X |
| 3,384,657 | 5/1968 | Weissberger et al. | 260/561 K X |

OTHER PUBLICATIONS

Angyal et al., CA 46:11113a, (1952).
Anderson et al., CA 67:68125h, (1967).

*Primary Examiner*—Thomas Waltz
*Attorney, Agent, or Firm*—A. W. Breiner

[57] ABSTRACT

A method is described for preparing an α-substituted-α-acylacetamide wherein an α-acyl-α-halo-acetamide is allowed to react with an organic compound with pKa between 7 and 12 in a medium of an aprotic solvent and in the presence of a tetraalkylguanidine as basic condensing agent.

7 Claims, No Drawings

PREPARATION OF α-ACYLACETAMIDES USING TETRAMETHYL GUANIDINE CONDENSING AGENT

The present invention relates to a new method for the preparation of 2-equivalent yellow forming colour couplers.

In the subtractive three-colour silver halide photography it is common practice to use colour couplers which upon colour development of the exposed photographic element couple with the oxidized developer, more particularly an aromatic primary amino compound, to form a cyan, magenta and yellow dyestuff image. For the formation of the yellow dyestuff image open-chain ketomethylene compounds are used, (cfr. Mees & James, The theory of the photographic process, 3rd Ed. 1966 p.388-389) preferably acylacetamides, e.g. acylacetanilides.

It is also known to employ yellow forming colour couplers wherein the methylene group is unsubstituted, thus requiring for the formation of one molecule of dyestuff the development of 4 molecules of exposed silver halide, and yellow forming colour couplers, wherein the methylene group carries a substituent that is split off upon colour development so that only two exposed silver halide molecules should be developed to form one molecule of dyestuff. The former compounds are known as 4-equivalent couplers whereas the latter are known as 2-equivalent couplers.

The principle advantages of 2-equivalent colour couplers are known. They require approximately half as much silver halide as the 4-equivalent couplers so that in the preparation of the silver halide elements less silver halide can be used and thinner emulsion layers can be employed, which results in improved resolution and sharpness.

In the prior art e.g. in French Pat. No. 1,411,384, 2-equivalent yellow forming colour couplers have been described the active methylene group of which carries aroxy groups more particularly phenoxy substituents. These 2-equivalent couplers are prepared by reaction of the corresponding coupler carrying at the coupling position (active methylene group) a chlorine atom, with phenols in a medium of acetonitrile in the presence of triethylamine as basic condensing agent. This method leads to the formation of many by-products so that isolation of the phenoxy-substituted coupler is difficult and low yields are obtained.

Other prior art 2-equivalent colour couplers for yellow carrying at the coupling position a nitrogen-containing heterocycle (see e.g. the published German patent application Nos. DOS 2,318,807, 2,329,587, 2,363,675 and 2,402,220) are prepared by reaction of the corresponding coupler having a chloro-substituted methylene group, with the appropriate heterocycle in an aprotic solvent e.g. dimethyl formamide, hexamethyl phosphoric triamide and dimethyl sulphoxide in the presence of an aliphatic amine e.g. triethylamine, a basic heterocycle e.g. pyridine or alkali salts of alcohols e.g. sodium methanolate as basic condensing agents. These methods too are accompanied with undesirable side-reactions.

It has now been found that 2-equivalent yellow forming acylacetamide colour couplers can be prepared with high yields and a high degree of purity by reaction of the corresponding acylacetamide coupler carrying at the coupling position (methylene group) a halogen atom, more particularly a chlorine atom, with an organic compound having an acid strength in terms of pKa between 7 and 12 (at 20° C.) in an aprotic solvent and in the presence of a tetraalkyl guanidine, more particularly tetramethyl guanidine as basic condensing agent.

The use of a tetraalkyl guanidine as basic condensing agent makes possible to introduce in the coupling position of the yellow forming couplers a large variety of organic substituents derived from organic compounds of varying acid strength including phenols (e.g. as decribed in the above French Patent) and heterocyclic compounds with acid NHgroups (e.g. as described in the published German Patent Applications referred to hereinbefore) representative examples of which are listed in the following table I.

Table I

| Compound | pKa (20° C) |
|---|---|
| CH₃CO—⟨phenyl⟩—OH | 8.05 |
| C₂H₅OCO—⟨phenyl⟩—OH | 8.47 |
| (imidazole-type structure with NH) | 10.1 |
| (triazole-type structure with NH) | 9.42 |
| (hydantoin-type structure with H₃C—N, O, N—CH₃) | 8.6 |
| (benzisoxazolinone-type with NH) | 10.69 |
| (quinazolinedione-type, O=, H—N) | 8.23 |
| (quinazolinone-type, O=, H—N) | 9.81 |

According to the method of the invention, the substitution proceeds very selectively so that little by-products are formed and higher yields are obtained than according to the prior art methods. The isolated reaction products have a high degree of purity.

The invention thus provides a method of preparing α-substituted -α-acylacetamides by reaction of an α-halo-α-acylacetamide, more particularly corresponding to the formula:

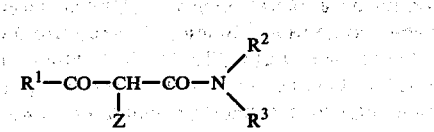

wherein $R^1$, $R^2$ and $R^3$ are groups of the type commonly present in acylacetamide couplers for yellow, and Z is a halogen atom, more particularly chlorine with an organic compound having a pKa between 7 and 12 in a medium of an aprotic solvent wherein the reaction occurs in the presence of a tetraalkyl guanidine, preferably tetramethyl guanidine as basic condensing agent.

$R^1$, $R^2$ and $R^3$ are any of the groups commonly present in acylacetamide couplers for yellow e.g. colour couplers of the type described in U.S. Pat. Nos. 3,056,675 — 3,369,899 — 3,393,040 — 3,393,041 — 3,409,439 — 3,619,190 — 3,645,742 — 3,660,095 and 3,725,072, in Belgian Pat. No. 717,841 and in the published German patent application Nos. 2,002,378 — 2,114,576 — 2,114,577 and 2,114,578.

More particularly $R^1$, $R^2$ and $R^3$ can represent one of the following groups:

$R^1$ a straight-chain or branched-chain alkyl group, preferably comprising from 1 to 18 C-atoms, which in the case of a secondary or tertiary alkyl group is preferably linked to the carbonyl group by means of the secondary or tertiary C-atom, an alkoxy alkyl group, a dicycloalkyl group, a heterocycle or an aryl group, preferably a phenyl group which may carry one or more substituents: e.g. $C_1$-$C_{18}$ alkyl, $C_1$-$C_{18}$ alkoxy, aralkyl, aryl, aroxy, sulpho, carboxy, halogen e.g. chlorine, bromine and fluorine, acyl, acyloxy, acylamino, sulphonamido, amino, carbamoyl, or sulphamoyl, which may be substituted by alkyl, aryl, aralkyl or a heterocycle, $R^2$ hydrogen or a $C_1$-$C_5$ alkyl group, e.g. methyl, and $R^3$ $C_1$-$C_{18}$ alkyl, a heterocycle e.g. 2-thiazolyl, or preferably aryl e.g. phenyl which may be substituted by one or more substituents: e.g. $C_1$-$C_{18}$ alkyl, $C_1$-$C_{18}$ alkoxy, halogen e.g. chlorine, bromine and fluorine, sulpho, carboxy, aryl, aralkyl, aroxy, acyl, acyloxy, acylamino, sulphonamido, amino, carbamoyl or sulphamoyl groups which may be substituted by alkyl, aryl, aralkyl or a heterocycle.

The 2-equivalent colour couplers prepared according to the method of the present invention are naturally preferably derived from the prior art colour couplers having excellent properties as regards absorption characteristics and stability of the dyes formed upon colour development.

Pivaloylacetanilides and benzoylacetanilides, especially o-alkoxy benzoylacetanilides, are preferred which may carry in the anilide part one to three substituents of the type referred to hereinbefore preferably in the 2-, 4- and 5-positions.

In the method according to the present invention the couplers with chloro-substituted methylene group and the compounds with acid strength in terms of pKa between 7 and 12 are generally employed in equimolar amounts although the latter compounds can be used in excess.

The tetramethyl guanidine can be used in equimolar amounts with respect to the compound with pKa between 7 and 12. However, it is preferred to use a molar ratio of tetramethyl guanidine to compound with pKa between 7 and 12, of 2 or more.

The substitution reaction generally occurs by boiling the reaction partners in a suitable aprotic solvent e.g. acetonitrile, ethers, dimethylformamide, dioxan, etc. although it is possible to use lower temperatures. The amount of solvent is not critical and depends on the solubility of the reaction partners therein.

The 2-equivalent yellow-forming colour coupler prepared according to the method of the present invention can be isolated from the reaction medium in the usual way by pouring the reaction mixture into water, acetic acid or diluted sulphuric acid and recrystallizing to obtain the colour coupler with a high degree of purity. For some compounds recrystallization is preceded by an extraction step.

Representative examples of 2-equivalent colour couplers made according to the method of the present invention are listed in the following table. Other representative examples can be found in U.S. Ser. No. 635,064, now U.S. Pat. No. 4,032,347, filed on even date herewith. The preparation method is illustrated by means of the preparations given hereinafter.

TABLE

| Colour coupler | melting point °C | yield % |
|---|---|---|
| 1. (structure with $H_3C-C(CH_3)_2-CO-CH-CONH-$ aryl-$OC_{16}H_{33}$, $SO_2N(CH_3)_2$, with triazole N-substituent) | 80 | 72 |
| 2. (structure with $OC_{16}H_{33}$-aryl-$CO-CH-CONH-$ aryl-$OCH_3$, $SO_2CH_3$, with triazole N-substituent) | 100 | 58 |

TABLE-continued

| Colour coupler | melting point °C | yield % |
|---|---|---|

3. [Structure: 2-hexadecyloxyphenyl-CO-CH(N-heterocycle)-CONH-(2-methoxy-4-methoxycarbonylphenyl); heterocycle is 1,3-dimethyl-2,4-dioxo-imidazoline fused system] — 94, 77

4. [Structure: 2-hexadecyloxyphenyl-CO-CH(N-heterocycle)-CONH-(2-methoxy-5-methylsulfonylphenyl); heterocycle is 4-oxo-quinazoline] — 120, 46

5. [Structure: (CH₃)₃C-CO-CH(N-heterocycle)-CONH-(3-hexadecyloxy-4-... dimethylsulfamoylphenyl); heterocycle is 4-oxo-quinazoline] — 95, 80

6. [Structure: 2-hexadecyloxyphenyl-CO-CH(O-C₆H₄-R)-CONH-(2-methoxy-5-methylsulfonylphenyl)]
   a) R = COCH₃
   b) R = COOCH₃
   — 106, 72 / 116, 57

7. [Structure: 2-hexadecyloxyphenyl-CO-CH(O-C₆H₄-R)-CONH-(2,5-dimethoxy-4-dimethylsulfamoylphenyl)]
   a) R = COCH₃
   b) R = COOCH₃
   — 100, 43 / 122, 72

TABLE-continued

| Colour coupler | melting point °C | yield % |
|---|---|---|
| 8. 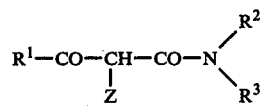 | 80 | 50 |

Preparation 1: compound 1

To a solution of 3.5 g (0.05 mole) of 1.2.4-triazole and 13 ml (0.1 mole) of tetramethyl guanidine in 150 ml of acetonitrile, 30 g (0.05 mole) of α-chloro-α-pivaloyl-(2′-hexadecyloxy-5′-N,N-dimethylsulphamoly)-acetanilide were added. The mixture was refluxed for 2 hours and then acidified by means of acetic acid. The mixture was poured into water and the oil obtained was extracted with ethylacetate. After drying, the organic solvent was removed by evaporation and the residual oil recrystallized from a mixture of methanol and hexane (7:3). Yield: 23 g (72%). Melting point: 80° C.

Preparation 2: compound 7b

To a solution of 204 g (0.3 mole) of α-chloro-α-(2-hexadecyloxy)benzoyl-(2′,5′-dimethoxy-4′-N,N-dimethylsulphamoyl) acetanilide and 46.5 g (0.3 mole) of p-hydroxy benzoic acid methylester in 900 ml of acetonitrile, 78 ml (0.6 mole) of tetramethyl guanidine were added whereupon the mixture was boiled for 7 hours. After cooling, 500 ml of water were added and the mixture was acidified with 6 N sulphuric acid. The precipitate was filtered off by suction and recrystallization from ethanol. Yield: 172 g (72%). Melting point: 122° C.

We claim:

1. Method for the preparation of an α-substituted-α-acylacetamide by reaction of an α-acyl-α-halo-acetamide with an organic compound with an acid strength in terms of pKa between 7 and 12 in a medium of an aprotic solvent, characterised in that the reaction occurs in the presence of a tetramethyl guanidine as basic condensing agent.

2. Method according to claim 1, wherein the α-acyl-α-halo-acetamide corresponds to the formula:

$$R^1-CO-CH-CO-N<^{R^2}_{R^3}$$
$$\quad\quad\quad\quad\;\;|$$
$$\quad\quad\quad\quad\;Z$$

wherein
Z is halogen, and
each of $R^1$, $R^2$ and $R^3$ are substituents of the type commonly present in acylacetamide colour couplers for silver halide colour photography.

3. Method according to claim 2, wherein $R^1$ represents an alkyl group, or an aryl group,
$R^2$ represents hydrogen, or $C_1$–$C_5$ alkyl, and
$R^3$ represents alkyl, or an aryl group.

4. Method according to claim 3, wherein the α-halo-α-acylacetamide is a benzoylacetanilide or pivaloylacetanilide the active methylene group of which carries a halogensubstituent.

5. Method according to claim 1, wherein the aprotic solvent is acetonitrile.

6. Method according to claim 1, wherein the reaction partners are used in equimolar ratios.

7. Method according to claim 1, wherein the molar ratio of tetramethyl guanidine to compound with pKa between 7 and 12 is 2.

* * * * *

UNITED STATES PATENT AND TRADEMARK OFFICE
CERTIFICATE OF CORRECTION

PATENT NO. : 4,131,735  Page 1 of 2
DATED : December 26, 1978
INVENTOR(S) : Raphael K. Van Poucke et al It is certified that error appears in the above-identified patent and that said Letters Patent is hereby corrected as shown below:

In the Heading, please insert

-- [30] Foreign Application Priority Data
    Jan 30, 1975   [GB]   United Kingdom  ..... 313/75 --

In the Specifications:

Column 2, Lines 35-40, part of Table I set forth as

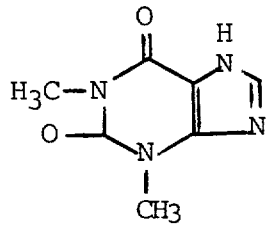   should read   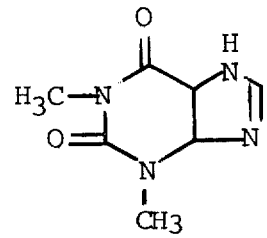

UNITED STATES PATENT AND TRADEMARK OFFICE
CERTIFICATE OF CORRECTION

PATENT NO. : 4,131,735
DATED : December 26, 1978
INVENTOR(S) : Raphael K. Van Poucke et al It is certified that error appears in the above-identified patent and that said Letters Patent is hereby corrected as shown below:

Column 7, Formula 8, part set forth as

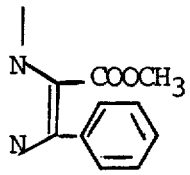   should read   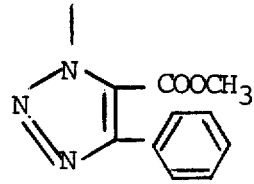

In the Claims:

Column 8, Line 38, Claim 4 "halogensubstituent" should read
-- halogen-substituent --

Signed and Sealed this

Seventeenth Day of January 1984

[SEAL]

Attest:

GERALD J. MOSSINGHOFF

Attesting Officer    Commissioner of Patents and Trademarks